(12) United States Patent
Newman (10) Patent No.: US 11,567,345 B2
(45) Date of Patent: Jan. 31, 2023

(54) WEARABLE DEVICE FOR COMMUNICATION WITH AN OPHTHALMIC DEVICE

(71) Applicant: MENICON SINGAPORE PTE LTD., Singapore (SG)

(72) Inventor: Stephen D. Newman, Singapore (SG)

(73) Assignee: MENICON SINGAPORE PTE LTD., Singapore (SG)

( * ) Notice: Subject to any disclaimer, the term of this patent is extended or adjusted under 35 U.S.C. 154(b) by 513 days.

(21) Appl. No.: 16/353,173

(22) Filed: Mar. 14, 2019

(65) Prior Publication Data

US 2019/0285911 A1 Sep. 19, 2019

Related U.S. Application Data

(60) Provisional application No. 62/642,964, filed on Mar. 14, 2018.

(51) Int. Cl.
*G02C 7/04* (2006.01)
*A61B 5/00* (2006.01)
(Continued)

(52) U.S. Cl.
CPC .......... *G02C 7/04* (2013.01); *A61B 3/16* (2013.01); *A61B 5/6821* (2013.01); *A61F 2/16* (2013.01);
(Continued)

(58) Field of Classification Search
CPC .......... G02C 7/04; G02C 7/049; G02C 7/047; G02C 7/048; G02C 2202/22; G02C 7/021; G02C 7/022; G02C 7/06; G02C 7/083; G02C 2202/16; G02C 2202/24; G02C 7/027; G02C 7/028; G02C 7/046; G02C 2202/06; G02C 7/024; G02C 7/041; G02C 7/042; G02C 7/044; G02C 7/061; G02B 1/043; G02B 27/0025; G02B 27/0075;
(Continued)

(56) References Cited

U.S. PATENT DOCUMENTS 8,857,983 B2 10/2014 Pugh et al.
9,289,123 B2 3/2016 Weibel et al.
(Continued)

FOREIGN PATENT DOCUMENTS

EP 2851738 A3 5/2015
EP 2876487 A1 5/2015
KR 20170140774 A 12/2017

OTHER PUBLICATIONS

International Search Report and Written Opinion for PCT Application No. PCT/SG2019/050140, dated Jul. 8, 2019.
(Continued)

*Primary Examiner* — William R Alexander
*Assistant Examiner* — Sharrief I Broome
(74) *Attorney, Agent, or Firm* — Dorsey & Whitney LLP (57) ABSTRACT

A system can include an aural computing system in communication with the ophthalmic device. In some embodiments, the aural computing system can include a wireless communication device in communication with the ophthalmic device. In some embodiments, the ophthalmic device comprises a contact lens, which can inserted into the user's eye. The wireless communication device can comprise wearable technology.

25 Claims, 8 Drawing Sheets

(51) Int. Cl.
| | |
|---|---|
| *A61F 2/16* | (2006.01) |
| *A61B 3/16* | (2006.01) |
| *H04R 1/10* | (2006.01) |
| *A61F 9/00* | (2006.01) |
| *G02C 11/00* | (2006.01) |
| *G08B 5/22* | (2006.01) |
| *G08B 21/18* | (2006.01) |
| *G02C 7/08* | (2006.01) |
| *A61B 5/02* | (2006.01) |
| *G06F 3/01* | (2006.01) |
| *A61B 3/10* | (2006.01) |
| *A61B 5/145* | (2006.01) |

(52) U.S. Cl.
CPC .......... *A61F 2/1613* (2013.01); *A61F 9/0008* (2013.01); *G02C 11/10* (2013.01); *G08B 5/22* (2013.01); *G08B 21/182* (2013.01); *H04R 1/10* (2013.01); *A61B 3/101* (2013.01); *A61B 5/02* (2013.01); *A61B 5/14532* (2013.01); *A61F 2250/0002* (2013.01); *A61F 2250/008* (2013.01); *G02C 7/083* (2013.01); *G06F 3/013* (2013.01)

(58) Field of Classification Search
CPC .... G02B 27/4205; G02B 3/00; G02B 5/1828; G02B 1/041; G02B 2027/0123; G02B 27/0037; G02B 27/0172; G02B 27/4211; G02B 3/0081; G02B 5/18; G02B 5/1895; G02B 2027/015; G02B 5/30; G02B 1/04; G02B 5/20; G02B 1/115; G02B 1/18; A61F 2/16; A61F 2/1613; A61F 2/1648; A61F 2250/0002; A61F 2/14; A61F 2/1624; A61F 2/1627; A61F 2/1635; A61F 9/0017; A61F 2002/1699; A61F 2240/001; A61F 2250/0053; A61F 2/142; A61F 2/145; A61F 2/1618; A61F 2/1637; A61F 2002/0894; A61F 2002/1681; A61F 2002/1696; A61F 2002/16965; B29D 11/00038; B29D 11/00048; B29D 11/00125; B29D 11/00009; B29D 11/00317; B29D 11/0048; B29D 11/00105; B29D 11/00346; B29D 11/00567; B29D 11/00634; B29D 11/00644; B29D 11/00923; B29D 11/00; B29D 11/00057; B29D 11/00067; B29D 11/00076; B29D 11/00134; B29D 11/00182; B29D 11/00192; B29D 11/00221; H01L 2224/13109; H01L 2924/00014; H01L 2924/0105; H01L 2924/01083; H01L 2924/013; H01L 2924/20105; H01L 2224/11312; H01L 2224/16225; H01L 2224/2919; H01L 2224/32225; H01L 2224/73204; H01L 2224/81203; H01L 2224/83203; H01L 2924/10253; H01L 2224/05599; H01L 2224/83104; H01L 2924/00; H01L 2924/00012; H01L 2924/00013; H01L 2924/0665; A61L 31/10; A61L 2430/16; A61L 29/085; A61L 2300/404; A61L 27/54; A61L 12/086; A61L 12/12; A61L 12/124; A61L 12/142; A61L 12/143; A61L 12/145; A61L 2300/202; A61L 2300/208; A61L 2300/606; A61L 2400/10; A61L 2400/12; A61L 2420/02; A61L 2420/08; A61L 27/025; A61L 27/16; B29C 39/26; B29C 33/40; B29C 39/006; B29C 2045/0027; B29C 33/0016; B29C 33/0022; B29C 33/303; B29C 33/42; B29C 33/424; B29C 39/02; B29C 39/12; B29C 39/146; B29C 39/18; B29C 39/24; B29C 45/0025; B29C 45/0081; B29C 45/2708; B29C 45/372; B29C 45/572; B29C 67/246

See application file for complete search history.

(56) References Cited

U.S. PATENT DOCUMENTS

| | | | |
|---|---|---|---|
| 9,332,935 B2 | 5/2016 | Etzkorn et al. | |
| 2004/0156021 A1* | 8/2004 | Blum | A61B 3/0285 351/233 |
| 2010/0249548 A1* | 9/2010 | Muller | A61B 5/14532 600/318 |
| 2012/0235886 A1* | 9/2012 | Border | G06F 3/017 345/8 |
| 2014/0005514 A1 | 1/2014 | Pugh et al. | |
| 2015/0018781 A1* | 1/2015 | Rinderknect | A61B 5/0082 604/298 |
| 2015/0063605 A1 | 3/2015 | Pugh | |
| 2015/0065837 A1 | 3/2015 | Abreu | |
| 2015/0065905 A1 | 3/2015 | Pugh | |
| 2016/0051184 A1 | 2/2016 | Wisbey et al. | |
| 2017/0007450 A1 | 1/2017 | Samec et al. | |
| 2017/0024555 A1* | 1/2017 | Flitsch | G06F 21/32 |
| 2017/0026790 A1* | 1/2017 | Flitsch | A61B 5/681 |
| 2017/0047051 A1* | 2/2017 | Deering | G09G 5/391 |
| 2017/0097520 A1* | 4/2017 | Lee | G02C 7/04 |
| 2017/0097524 A1* | 4/2017 | Honore | G02C 11/10 |
| 2017/0112433 A1* | 4/2017 | Pugh | G01J 1/42 |
| 2017/0255026 A1* | 9/2017 | Rakhyani | G01R 33/032 |
| 2017/0358942 A1* | 12/2017 | Pugh | A61B 5/742 |
| 2018/0039097 A1* | 2/2018 | Gutierrez | G02C 7/083 |
| 2018/0063625 A1 | 3/2018 | Boesen et al. | |

OTHER PUBLICATIONS

Extended European Search Report for EP Application No. 19767424, dated Dec. 2, 2021.

\* cited by examiner

WEARABLE DEVICE FOR COMMUNICATION WITH AN OPHTHALMIC DEVICE

CROSS-REFERENCE TO RELATED APPLICATIONS

The present application claims priority from U.S. Provisional Application No. 62/642,964 filed on Mar. 14, 2018, the disclosure of which is incorporated herein, in its entirety, by this reference.

BACKGROUND

Wearable technology is widely used to track various biometrics. The biometrics are related to things such as length of exercise, heart rate, and number of steps a user experiences. Traditional biometrics, however, rarely provide insight into the actual health of the wearer. For example, the wearable technology cannot track a blood sugar level or red blood cell count.

The eye is subject to numerous diseases and ailments that can be treatable with early detection. Some of these conditions include increased intraocular pressure, glaucoma, *Acanthamoeba keratitis*, cataracts, conjunctivitis, corneal ulcer, dry eye syndrome, hyphema, and macular hole, to name a few. Some of these conditions can lead to blindness or even the loss of an eye. Some conditions can be easily detected, such as conjunctivitis, while others can require testing to diagnose.

Some diseases can be detected or tracked via the eye or tear fluid. For example, diabetes, hypertension, autoimmune disorders, high cholesterol, thyroid irregularities, and cancer can often be detected through the eye. For example, diabetes can be tracked through tear fluid. The tear fluid present in a diabetic person can be used to determine an amount of glucose in the diabetic person.

An example of a contact lens for measuring conditions of an eye is disclosed in U.S. Pat. No. 9,289,123 issued to Douglas Weibel. In this reference, an eye-mountable device for measuring an intraocular pressure is provided. The device can include a transparent polymeric material having a concave surface configured to be removably mounted over a corneal surface of an eye, an antenna, an expandable member, a sensor and control electronics at least partially embedded in the transparent polymeric material. The expandable device is configured to expand and apply a force to the corneal surface, and the sensor is configured to detect a resistance to deformation of the cornea in response to the applied force. The resistance to deformation of the cornea in response to the force applied by the expandable member is indicative of the intraocular pressure of the eye.

Another example of a contact lens for measuring a condition of an eye is disclosed in U.S. Pat. No. 9,332,935 issued to James Etzkorn. In this reference, body-mountable devices and methods for embedding a structure in a body-mountable device are described. A body-mountable device includes a transparent polymer and a structure embedded in the transparent polymer. The transparent polymer defines a posterior side and an anterior side of the body-mountable device. The structure has an outer diameter and an inner diameter and includes a sensor configured to detect an analyte and an antenna. The antenna includes a plurality of conductive loops spaced apart from each other between the outer diameter and the inner diameter.

Another example of a contact lens for measuring conditions of an eye is disclosed in U.S. Pat. No. 8,857,983 issued to Randall Braxton Pugh. In this reference, antennas and antenna systems are disclosed for incorporation into mechanical devices, including medical devices, such as ophthalmic devices, including contact lenses. These antennas and antenna systems can be utilized to transmit data from the mechanical device to a receiver, to receive data from a transmitter, and/or to inductively charge an electro-mechanical cell or the like incorporated into the mechanical device.

Each of these references is herein incorporated by reference for all that they contain.

SUMMARY

In one embodiment, a system for communicating with an ophthalmic device is described.

The system can include an aural computing system in communication with the ophthalmic device.

In some embodiments, the aural computing system can include a wireless communication device in communication with the ophthalmic device.

In some embodiments, the ophthalmic device can include a contact lens.

In some embodiments, the contact lens can include an insertable eye device.

In some embodiments, the ophthalmic device can include a body.

In some embodiments, the ophthalmic device can include an antenna coupled to the body.

In some embodiments, the ophthalmic device can include an energy source in communication with the antenna.

In some embodiments, the ophthalmic device can include a wireless transceiver in communication with the antenna.

In some embodiments, the ophthalmic device can include a sensor coupled to the body in communication with the wireless transceiver.

In some embodiments, the ophthalmic device can include an output device coupled to the body.

In some embodiments, the output device can hold a substance to administer to a user when the user is wearing the ophthalmic device.

In some embodiments, the aural computing system can trigger the output device to administer the substance to an eye of the user.

In some embodiments, a user communication device can be coupled to the body of the ophthalmic device.

In some embodiments, the user communication device can change a field of view of a user.

In some embodiments, the aural computing system can trigger the user communication device to change optical characteristics of the ophthalmic device.

In some embodiments, changing the optical characteristics can include displaying a message to the user.

In some embodiments, changing the optical characteristics can include changing a prescription of the contact lens based on usage.

In some embodiments, the aural computing system can include a wearable wireless device.

In some embodiments, the wearable device can include a processor module.

In some embodiments, the wearable device can include an antenna in communication with the processor module.

In some embodiments, the antenna can be in communication with the ophthalmic device.

In some embodiments, the system can include a second ophthalmic device.

In some embodiments, the aural computing system can communicate with the second ophthalmic device.

In some embodiments, the second ophthalmic device can communicate to a second aural device.

In some embodiments, the aural computing system further includes a wearable device securable to a head of a user.

In some embodiments, the aural computing system can further include an accelerometer.

In some embodiments, the accelerometer can detect a movement of the user when the wearable device is worn by the user and in response to a user movement.

In some embodiments, the aural computing system can change the optical characteristics of the ophthalmic device based on detections by the accelerometer.

In some embodiments, the aural computing system can gather and analyze data from the ophthalmic device.

In some embodiments, the aural computing device can transmit data to an external computing system.

In some embodiments, the external computing system can be a cloud computing system.

In some embodiments, the aural computing device and ophthalmic device are spaced at a substantially constant distance from each other when worn by a user.

In some embodiments, the aural computing device can be a wearable device and the ophthalmic device can be a contact lens worn by the user.

In some embodiments, the contact lens is embedded in the user's eye.

In some embodiments, the wearable device can be an ear piece.

In some embodiments, the ear piece can have a predetermined broadcast range.

In some embodiments, the predetermined broadcast range can be less than six inches.

In some embodiments, the ear piece can include a focused transmitter to direct transmissions towards an eye of the user when the ear piece is worn within an ear of the user.

In some embodiments, the ear piece includes a focused receiver to receive transmissions from the ophthalmic device when the ear piece is worn within an ear of the user and when the ophthalmic device is positioned on an eye of the user.

In another embodiment, a method of alerting a user is described.

The method can include receiving information from an ophthalmic device worn by a user, analyzing the information from the contact lens, and transmitting a message to the ophthalmic device of the user regarding the analyzed information, wherein the message triggers a change of an optical characteristic of the ophthalmic device.

In some embodiments, analyzing the information can include determining if predetermined thresholds are satisfied.

In some embodiments, the method can include alerting the user when the predetermined threshold is satisfied.

In some embodiments, the method can include requesting input from the user on performing a predetermined action.

In some embodiments, the predetermined action can include administering a substance to the user.

In some embodiments, the method can include alerting a user when a predetermined threshold is not satisfied.

In some embodiments, the method can include triggering a change of a prescription strength of the ophthalmic device.

In some embodiments, the triggering a change of an optical characteristic of the ophthalmic device, can include triggering a message display on the ophthalmic device within a field of view of the user.

In some embodiments, the method can include transmitting the analyzed information to a remote device.

In some embodiments, the remote device can be a cloud computing device.

In some embodiments, the method can include receiving a safety alert.

In some embodiments, the method can include transmitting the safety alert to a remote device associated with the user.

In some embodiments, the safety alert can include a location of the user and a safety message.

In another embodiment, a method of changing an ophthalmic device is described. The method can include receiving information from a wireless receiver worn by a user, analyzing the information from the wireless receiver, and prompting a change of an optical characteristic of the ophthalmic device based on the analyzing.

In some embodiments, the method can include detecting a movement of a user's head.

In some embodiments, prompting a change of an optical characteristic of the ophthalmic device can include prompting a change of a prescription strength of the ophthalmic device.

In some embodiments, the method can include requesting information from the ophthalmic device.

In some embodiments, the method can include analyzing the information from the ophthalmic device.

In some embodiments, the method can include prompting a change of an optical characteristic of the ophthalmic device based on the analyzing of information from the ophthalmic device.

In another embodiment, a contact lens system is described.

The contact lens system can include a first contact lens and a wearable wireless receiver in communication with the first contact lens.

The first contact lens can include a body and at least one sensor located in the body of the first contact lens.

In some embodiments, the wearable wireless receiver can be an ear piece.

In some embodiments, the first contact lens can include a directional transmitter located in the body of the first contact lens.

In some embodiments, the ear piece can include a directional receiver directed towards the contact lens.

In some embodiments, the first contact lens can include an antenna.

In some embodiments, the antenna can have a broadcast range of five inches or less.

In some embodiments, a processor module can be located in the body of the first contact lens in communication with the at least one sensor.

In some embodiments, an antenna can be located in the body of the first contact lens in communication with the at least one sensor.

In some embodiments, a battery can be located in the body of the first contact lens.

In some embodiments, the antenna can be in communication with the battery.

In some embodiments, the contact lens can be embedded in a user's eye and the wireless receiver can be an ear piece.

In some embodiments, the wireless receiver can be an ear piece with a predetermined broadcast range and a focused transmission direction.

In some embodiments, the predetermined broadcast range can be less than six inches.

In some embodiments, the contact lens can transmit raw data to the wireless receiver.

In some embodiments, the wireless receiver can be an ear piece and the contact lens can transmit information to the ear piece.

In another embodiment, an ear piece is described.

In some embodiments, the ear piece can include a speaker configured to generate an audible sound.

In some embodiments, the ear piece can include a transmitter in communication with a contact lens.

In some embodiments, the transmitter can include a directional receiver that receives signals from the direction of an eye of a user when the ear piece is mounted to the user's ear.

In some embodiments, the audible sound can include a message based on information sent from the contact lens.

In some embodiments, the information can include an intraocular pressure of an eye of a user.

In some embodiments, the information can include a glucose reading.

In some embodiments, the information can include a health condition.

In some embodiments, the information can include an eye dryness level.

In some embodiments, the information can include an eye strain level.

In some embodiments, the ear piece can include a processor to interpret a signal from a contact lens.

In some embodiments, the processor can send instructions to the contact lens in response to an interpretation of a signal from the contact lens.

In some embodiments, the instructions can include releasing a therapeutic agent into an eye from the contact lens.

In some embodiments, the instructions can include taking a measurement using the contact lens.

In some embodiments, the instructions can include changing an optical property of the contact lens.

In some embodiments, the processor can send the information from the contact lens to a remote device.

In some embodiments, the processor can modify the information from the contact lens prior to sending the information to the remote device.

In some embodiments, the remote device can be a personal mobile device.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

The principles described herein include incorporating a wireless receiver into an aural system that can communicate with an optical device. In some embodiments, the system can include aural computing system communicating with an ophthalmic device. In some embodiments, the aural computing system can be an ear piece set at a predetermined distance from the user's eye. The ophthalmic device can be a contact lens, glasses, sunglasses, prescription lenses, an implantable lens, another type of ophthalmic lens, or combinations thereof. The wireless receiver can receive and transmit data to the ophthalmic device.

Figure 1:
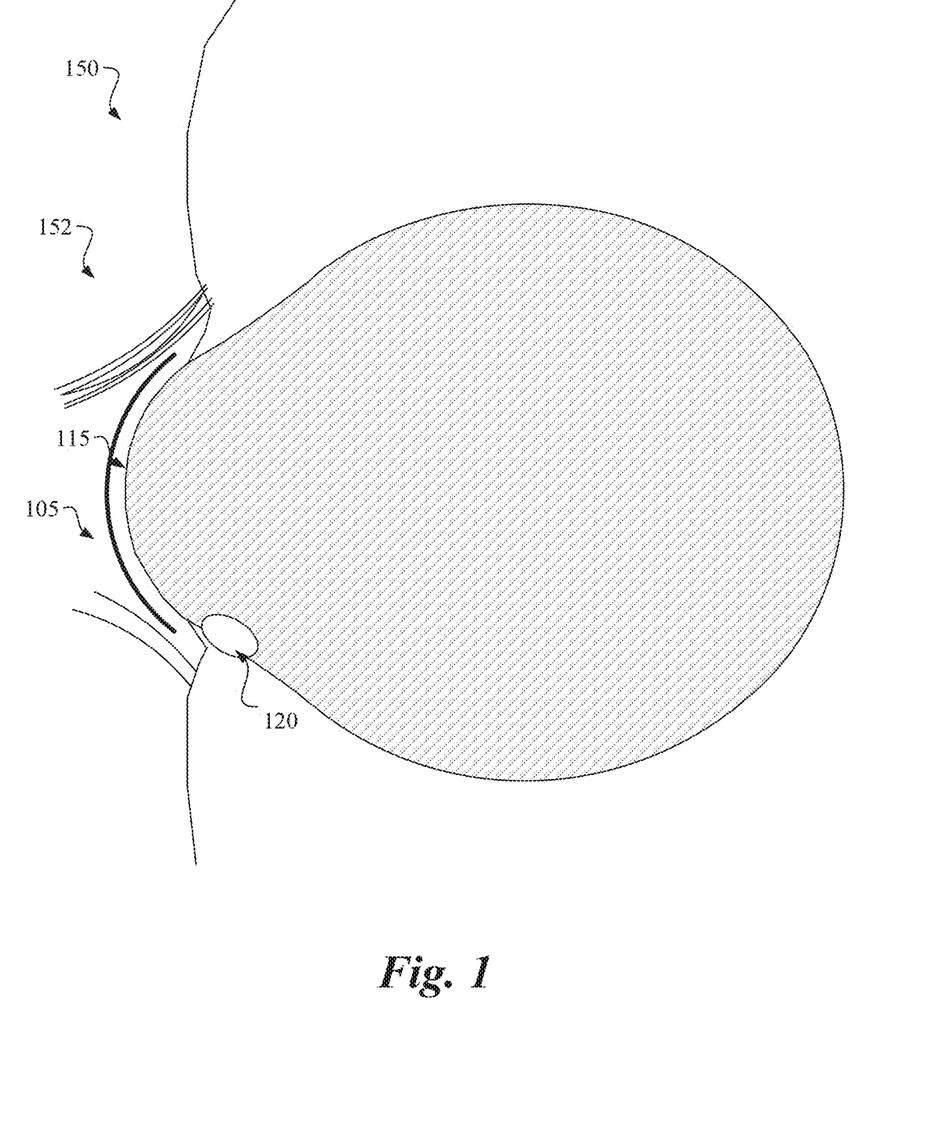
FIG. 1 illustrates an exemplary cross-sectional view of a contact lens positioned on an eye, in accordance with the present disclosure.

FIG. 1 depicts an example of a contact lens 105 disposed relative to a human eye 110. The contact lens 105 spans a portion of the exposed, outside, or distal surface of the eye 110, known as the cornea 115. The cornea 115 can be lubricated with tear fluid formed by the lacrimal gland 120. The contact lens 105 can contact the cornea 115 and be in contact with the tear fluid.

The contact lens 105 can be any appropriate type of contact lens. A non-exhaustive list of contacts lenses that can be compatible with the present disclosure include, but is not limited to, hard contact lenses, hydrogel lenses, silicone hydrogel lenses, extended wear contact lenses, spherical contact lenses, toric contact lenses, multifocal contact lenses, monovision contact lenses, rigid gas permeable lenses, toric lenses, orthokeratology lenses, another type of contact lens, or combinations thereof. In some embodiments, the contact lens 105 can incorporate a colored portion to change the appearance of a user's iris.

Other optical and structural properties of the contact lens 105 can be adjusted and/or fixed to produce a more comfortable and well performing contact lens 105. In some embodiments, the contact lens 105 includes a fixed base curve. In other words, the contact lens 105 can have the same volume of monomer and the same base curve across a wide range of powers. In some embodiments, the fixed base curve for the contact lens 105 across a range of powers is selected from within a range of from 7.50 to 9.10.

The contact lens 105 can include instruments to measure at least one parameter of the eye, eye lid, and/or tear fluid. In some examples, the contact lens includes a sensor to measure a constituent of the tear fluid. For example, the tear fluid can include a glucose level that can represent an indication of the user's diabetic condition. In another example, a sensor incorporated into the contact lens can measure an intraocular pressure of the eye. These measurements can be transmitted from the contact lens to a wearable device, such as an aural device located, worn, or disposed in or proximate to the user's ear.

Figure 2:
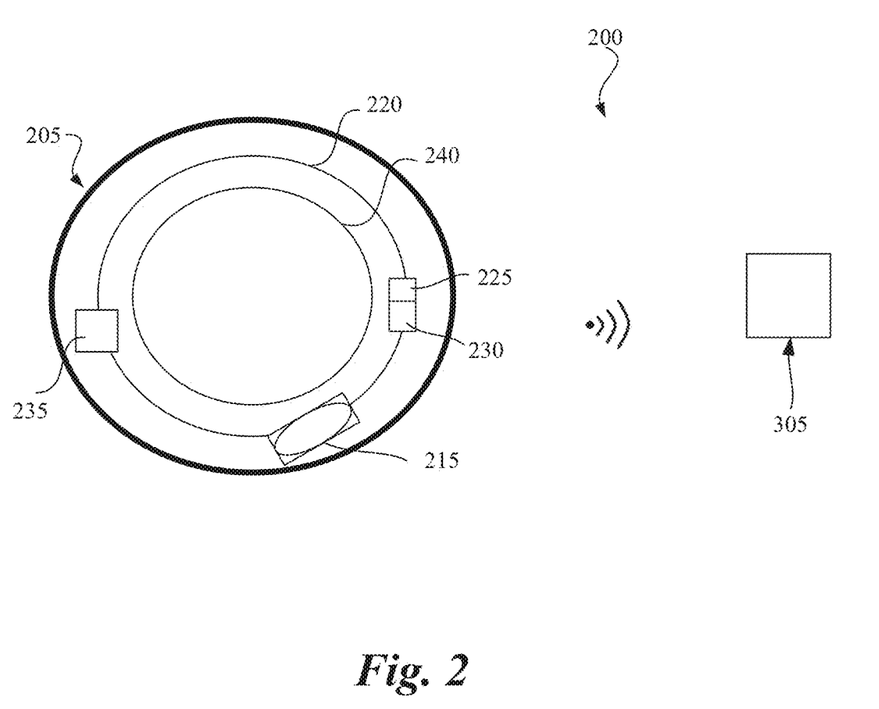
FIG. 2 illustrates an exemplary diagram of a system for communicating with an ophthalmic device, in accordance with the present disclosure

FIG. 2 depicts an example of a smart contact lens system 200. The smart contact lens system 200 can include a smart contact lens 205 and a wireless receiver 305. The smart contact lens 205 can include a series of integrated components offering a variety of capabilities. For example, the smart contact lens 205 can include a combination of a sensor 215, an antenna 220, an energy source 225, and a wireless transceiver 230. The smart contact lens 205 can include an output device 235 and a user communication device 240. According to one embodiment, the wireless receiver 305, the sensor 215, antenna 220, energy source 225, and wireless transceiver 230 are disposed in the contact lens outside the optic zone of the lens. Alternatively, one or more of the integrated components can be optically transparent, imperceptibly small, or otherwise appropriate for positioning within the optic zone of the lens.

The sensor 215 can detect a series of health conditions, ambient conditions, lens fit, and other biometric data. For example, the sensor can detect a series of biomarkers or lack thereof. The sensor 215 can detect ambient conditions such as lighting, humidity, wind force, ambient temperature, and so forth. Other conditions the sensor can detect include, but are in no way limited to, eye tracking, eye pressure, eye dryness, eye focusing conditions, light sensitivity, field loss, an ability to maintain eye contact, lens engagement force, lens location relative to the pupil, heart rate, pH, proteins/peptides, lipids, electrolytes, metabolites, pathogens, physiochemical parameters, other types of conditions, or combinations thereof. The sensor 215 can also detect various biomarkers indicative of other health conditions such as excessive glucose or insulin for diabetes or other markers indicative of ocular diseases or systemic diseases.

The output device 235 can include a reservoir that includes a substance, such as a therapeutic substance, that can be administered into the eye. In response to the detection of an eye condition or from an external source, the output device 235 can release at least a portion of the substance. Types of substances that can be released from the output device 235 can include, but are not limited to, insulin, hydrating substance, pain relievers, anti-inflammatory, eye lash enhancers, other types of substances, or combinations thereof. In some examples, the substance is a liquid. In yet other examples, the substance is a solid that can dissolve in the tear fluid.

The user communication device 240 can include any system configured to communicate with the user or alter the vision of the user. The user communication device 240 can change the optical characteristics of the contact lens 205. For example, the user communication device 240 can flash a visual communication in the user's field of vision. This can be a series of information available to the user and can include a simple message or a more complex message. For example, it can include simply flashing light or a color, or creating another visual variance to warn of a health condition or another type of condition. If a health condition is not present, the user communication device 240 can flash a first color such as a green color. An unhealthy condition can be indicated using a second color such as red. In some embodiments, the user communication device 240 can change the vision of the user. For example, if the user requires a changed prescription for driving, the user communication device 240 can alter the contact lens 205 to meet those requirements by dynamically modifying the shape, geometry, pressure, position, or visual aspects of the lens. If the user requires a setting for reading, the user communication device 240 can alter the contact lens 205 for reading. The user communication device 240 can respond to various detectable conditions to alter the field of view. In some embodiments, the user can also input requests or requirements for altering the field of view.

The antenna 220 can also be incorporated into the contact lens. In some examples, the antenna includes a signal transfer wire that can communicate with the wireless receiver 305. In other examples, the antenna can include a multiple loop antenna, a dipole antenna, a single pole antenna, another type of antenna, or combinations thereof.

The antenna structure 220 can include a loop or coil structure. In some examples, the antenna structure 220 can include conductive lines which include, for example, the coil or loop structure, as shown. The conductive lines can include the conductive material used to form the conductive layers described herein, and can have a line width of from about 25 micrometers to about 200 micrometers, or from about 50 micrometers to about 100 micrometers. In some examples the antenna structure 220 can be formed on an upper conductive layer, for example by printing conductive material in the form of the antenna structure 140. In some examples the antenna structure 220 can be formed by printing conductive material on the upper conductive layer, by any number of printing methods including, but in no way limited to tamp printing, inkjet printing, 3-D printing, and other suitable printing methods. The antenna structure 220 can also be formed by a stencil process wherein conductive material is painted or applied into a stencil including the desired antenna structure 220, which is disposed over the conductive layer. Other methods of forming the antenna structure 220 can be utilized as are known in the art or can be developed in the future. The antenna structure can have a thickness of from about 0.1 micrometers to about 20 micrometers, from about 0.5 micrometers to about 15 micrometers, or from about 1 micrometers to about 10 micrometers. In some examples the antenna structure 220 can thus be incorporated into, or become a part of the upper conductive layer after it has been deposited or formed. Once formed, the antenna structure can be encapsulated by a subsequent polymer layer, protecting the cornea from directly engaging the antenna structure 220 or any of the other smart contact lens 205 components.

The energy source 225 can include a battery. The battery can be rechargeable. The energy source 225 can initially have a stored charge or the energy source 225 can be charged by the optical sensor 265. The energy source 225 can include graphene. In some embodiments, the energy source 225 can be printed to a surface of the contact lens. The energy source 225 can be graphene printed battery. In some embodiments, the energy source 225 can be fully printable, can include a planar architecture. In some embodiments, the energy source 225 can be flexible and have an appropriately long shelf-life. The energy source 225 can operate in a moist environment that is exposed to the tear fluid. In some embodiments, the energy source 225 can have approximately one microampere per square millimeter capacity per unit area. The energy source 225 can include approximately twenty-five microampere per cubic centimeter capacity per unit volume.

The components can be printed or otherwise affixed to either the inner or outer surface of the contact lens 205. In some embodiments, the components can be sandwiched between various layers of the contacts lens 205. The components of the contact lens 205 can function while be submerged in a liquid. In other embodiments, the components can be prevented from contacting liquid by being sealed or encapsulated within the contact lens 205. The components can also be positioned on various layers of the contact lens 205, while still being communicatively connected.

The wireless receiver 305 can be located at any appropriate location. In some examples, the wireless receiver is incorporated into an ear-based device that can be worn by the user. In some examples, the wireless receiver 305 can be worn in or proximate to the user's ear. In those examples where the wireless receiver 305 can be positioned in the user's ear, the wireless receiver can be located at a consistent distance from the contact lens. Being located at a consistent distance from the contact lens allows for the wireless transmitter of the contact lens to be constructed to have a short broadcasting range, which means smaller and/or fewer components can need to be incorporated into the contact lens. Thus, a wireless receiver positioned consistently at a short distance of less than 12.0, and preferably less than 6.0 inches enables the design and construction of the contact lens to be simpler. In contrast, when the wireless transmitter is incorporated into a mobile device carried by the user, the distance of the mobile device from the contact lens can vary. For example, in one instance, the mobile device can be located proximate the user's head, such as when the user is speaking into the mobile device, while in other instances the mobile device can be left in an adjacent room or borrowed by another person. Thus, the contact lenses constructed to directly communicate with the mobile device would need to have a wireless transmitter that could accommodate for such a wide varying range. Meeting desired size and weight parameters in the contact lens can be achieved by placing the wireless receiver in a user's ear because the distance between the contact lens and the ear is consistent. The consistent distance can allow targeted and predictable transmission requirements. The targeted and predictable transmission requirements can allow a reduced size and weight of the components incorporated into the contact lens. This can provide a light weight or less complex contact lens and/or can provide additional space to incorporate more sensors or other components into a body of the contact lens. Further, in some examples, the contact lenses can be daily disposable contact lens or contact lenses that are replaced on a periodic basis. The targeted transmission and predictable transmission requirements can reduce a cost associated with manufacturing the contact lens. Each of the contact lens can be constructed to communicate with the contact lens at a short space protocol.

In some examples, if the spatial relationship between the contact lens and the wireless receiver is consistent, as is the case when the wireless receiver is consistently and predictably located in the user's ear, then the contact lens can be enabled to limit its transmissions to a single direction. This can also reduce the energy demands on the components of the contact lens.

Figure 3:
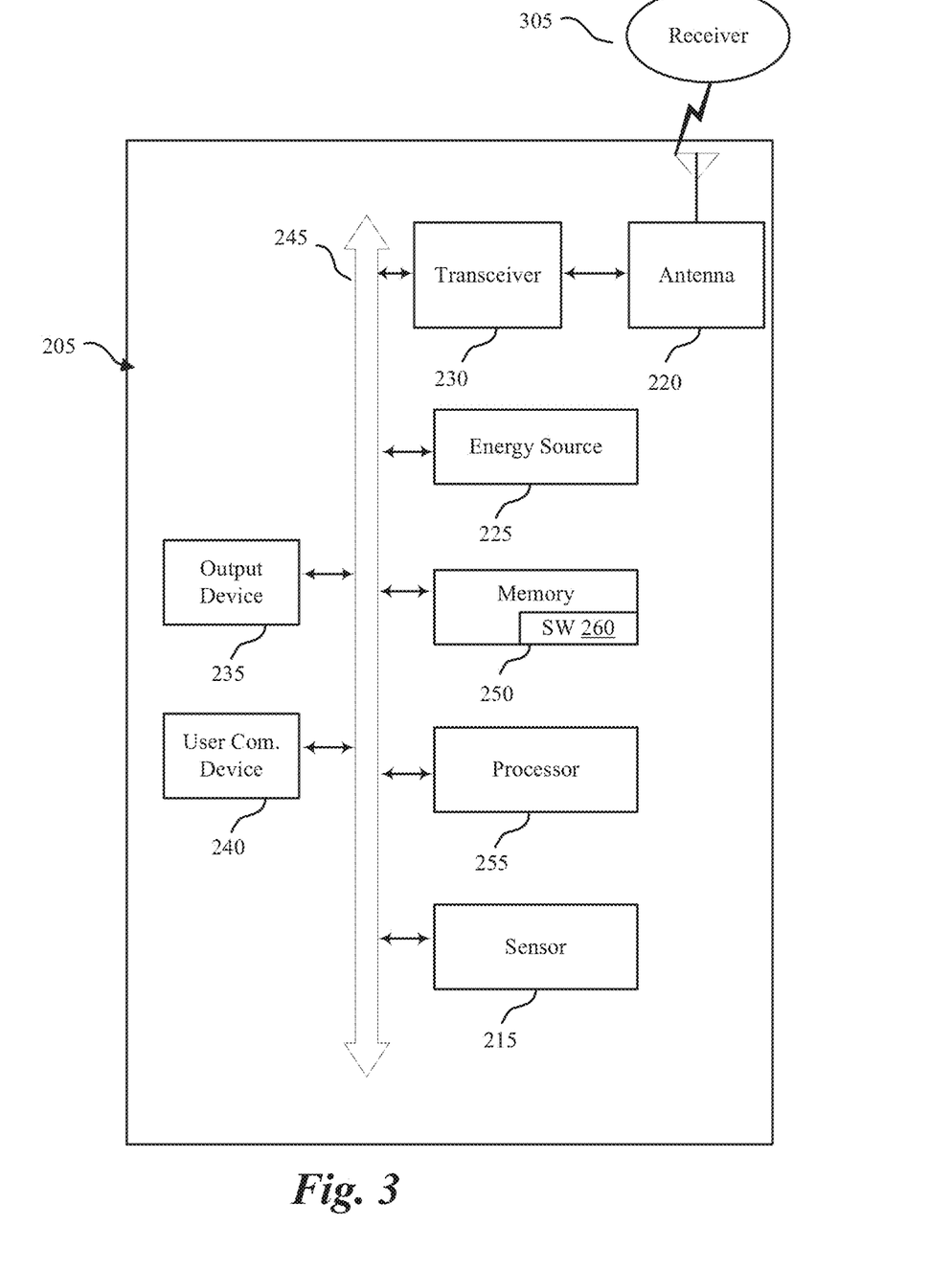
FIG. 3 illustrates an exemplary block diagram of an ophthalmic device, in accordance with the present disclosure.

A block diagram of the contact lens 205 is shown in FIG. 3. The contact lens 205 can include an antenna 220, an energy source 225, an output device 235, a user communication device 240, and at least one sensor 215. In some embodiments, the contact lens 205 can also include a transceiver module 230, a memory 250, a processor module 255, and/or a data bus 245.

The transceiver module 230 can communicate bi-directionally—via the one antenna 220 and/or wireless links—with the wireless receiver 305. For example, the transceiver module 230 can receive communications from and/or communicate bi-directionally with one or more smart contact lens to the wireless receiver 305. The transceiver module 230 can modulate packets to send to the antenna 220 for transmission. The packets can include communications regarding a health status, ambient condition, fit, pressure, lens location, or other tracked parameters detected by the smart contact lens 205. In some embodiments, the transceiver 345 can be a directional transceiver. The directional transceiver can transmit a message a distance of less than six inches. In some embodiments, the directional transceiver can transmit a message a distance of five inches or less.

In some embodiments, one element of the smart contact lens 205 (e.g., antenna 220, transmitter 230) can provide a connection using wireless techniques, including digital cellular telephone connection, Cellular Digital Packet Data (CDPD) connection, digital satellite data connection, and/or another connection. The signals associated with smart contact lens 205 can include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The antenna 220 and/or transmitter 230 can include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB).

One or more data buses 245 can allow data communication between one or more elements of the contact lens 205 (e.g., processor 255, output device 235, user communication device 240, memory 250, etc.).

The memory 250 can include random access memory (RAM), read only memory (ROM), flash RAM, and/or other types. The memory 250 can store computer-readable, computer-executable software/firmware code 260 including instructions that, when executed, cause the processor module 255 to perform various functions described in this disclosure (e.g., receiving an alert concerning biomarker presence or lack thereof, communicating an alert to the user, dispensing a substance to the user via the output device 235, communicating or altering a field of view for the user via the user communication device 240, and similar processor executed functions).

Figure 4:
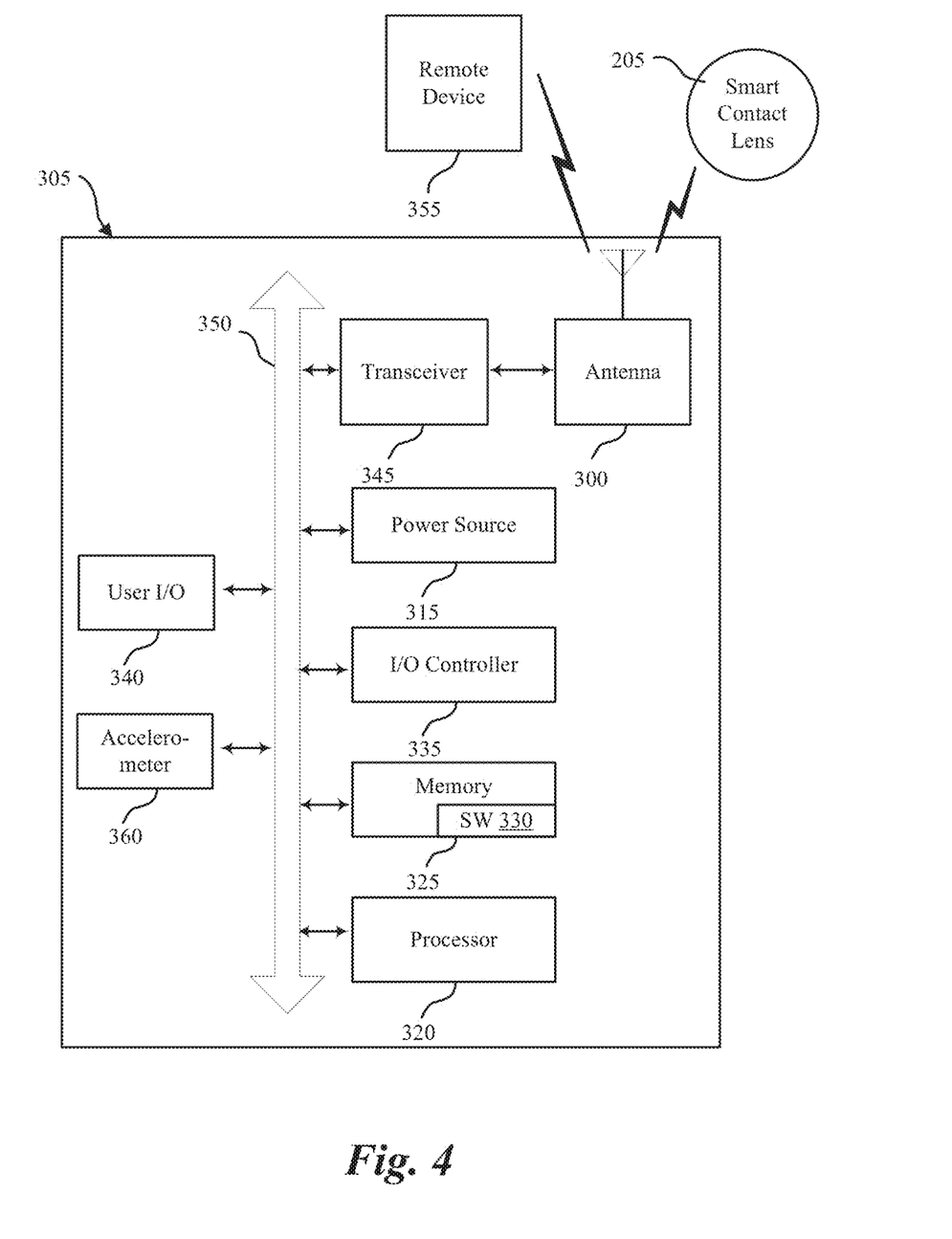
FIG. 4 illustrates an exemplary block diagram of an aural computing system, in accordance with the present disclosure.

An embodiment of the wireless receiver 305 is shown in FIG. 4. The wireless receiver 305 can include an antenna 310, a power source 315, and accelerometer 360. The wireless receiver 305 can also include a processor module 320, and memory 325 (including software/firmware code (SW) 330), an input/output controller module 335, a user input/output module 340, a transceiver module 345, and one or more antennas 310—each of which can communicate—directly or indirectly—with one another (e.g., via one or more buses 350). The transceiver module 345 can communicate bi-directionally—via the one or more antennas 300 and/or wireless links—with the smart contact lens 205. For example, the transceiver module 345 can receive communications from and/or communicate bi-directionally with one or more smart contact lens 205. In some embodiments, the transceiver module 345 can communicate bi-directionally with a remote device 355. The remote device 355 can include a mobile device, laptop, or other device. The transceiver module 345 can modulate packets to send to the one or more antennas 300 for transmission, and to demodulate packets received from the one or more antenna 310. While the wireless receiver 305 can include a single antenna 310, the wireless receiver 305 can also have multiple antennas 310 capable of concurrently transmitting or receiving multiple wireless transmissions. In some embodiments, the transceiver 345 can be a directional transceiver.

In some embodiments, the wireless receiver 305 can communicate with the contact lens using the communication protocols discussed previously. In further embodiments, the wireless receiver 305 can also communicate with a remote device 355. In some embodiments, the wireless receiver 305 can alternatively connect to a remote device 355 via a wired transmission. In some embodiments, one element of the wireless receiver 305 (e.g., one or more antennas 310, transceiver module 345, etc.) can provide a connection using wireless techniques, including digital cellular telephone connection, Cellular Digital Packet Data (CDPD) connection, digital satellite data connection, and/or another connection. The signals associated with wireless receiver 305 can include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 310 and/or transceiver module 345 can include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 310 can receive signals or information specific to and/or that can or cannot be exclusive to itself.

In some embodiments, the user input output module 340 can include an audio device, such as an external speaker system, a visual display, and/or an input device. A speaker can provide an audible output when one or more biomarkers are or are not present and/or has reached a predetermined threshold. For example, once a biomarker is present or has reached a predetermined threshold as detected by the at least one sensor (e.g., sensor 215), the wireless receiver 305 can receive a communication from the sensor 215 and can sound an audible alert to the user. In some embodiments, a visual display such as a screen or light can additionally and/or alternatively alert the user of the unhealthy condition. In some embodiments, the wireless receiver 305 can also vibrate or provide another tactile output to alert the user.

In some embodiments, the wireless receiver 305 can further communicate the unhealthy condition to a remote device 345. The remote device 345 can continue to alert the user, or others, along with the wireless receiver 305 of the unhealthy condition.

In other embodiments, the contact lens 205 can communicate ambient or other types of information to the wireless receiver 305. For example, the contact lens 205 can communicate a dryness of the eyes, a body temperature, a weather condition (cloudy, sunny, etc.), computer or technology usage, optical pressure, lens fit, friction detection, lens position, and other signal based information.

The accelerometer 360 can track movement information regarding the wireless receiver 305. For example, if the wireless receiver 305 is worn on the head (i.e., an ear or earring), the wireless receiver 305 can detect movement or orientation of the user's head. From this information, the wireless receiver 305 can deduce that the user is reading or performing another task when the user is looking down. Input from the accelerometer can also assist the wireless receiver 305 determine when user is driving, walking, running, traveling, or moving in some other way. The wireless receiver 305 can also determine if the user has experienced a head trauma and various ocular indicators need to be tracked for a potential concussion. In some embodiments, the wireless receiver 305 can change the optical characteristics of an ophthalmic device based on the detections by the accelerometer.

One or more buses 350 can allow data communication between one or more elements of the wireless receiver 305 (e.g., processor module 320, memory 320, I/O controller 335, user interface module 340, accelerometer 360, etc.).

The memory 325 can include random access memory (RAM), read only memory (ROM), flash RAM, and/or other types. The memory 325 can store computer-readable, computer-executable software/firmware code 330 including instructions that, when executed, cause the processor module 320 to perform various functions described in this disclosure (e.g., receiving an alert concerning biomarker presence, communicating an alert to the user, requesting information from the ophthalmic device, and similar processor based functions).

Figure 5:
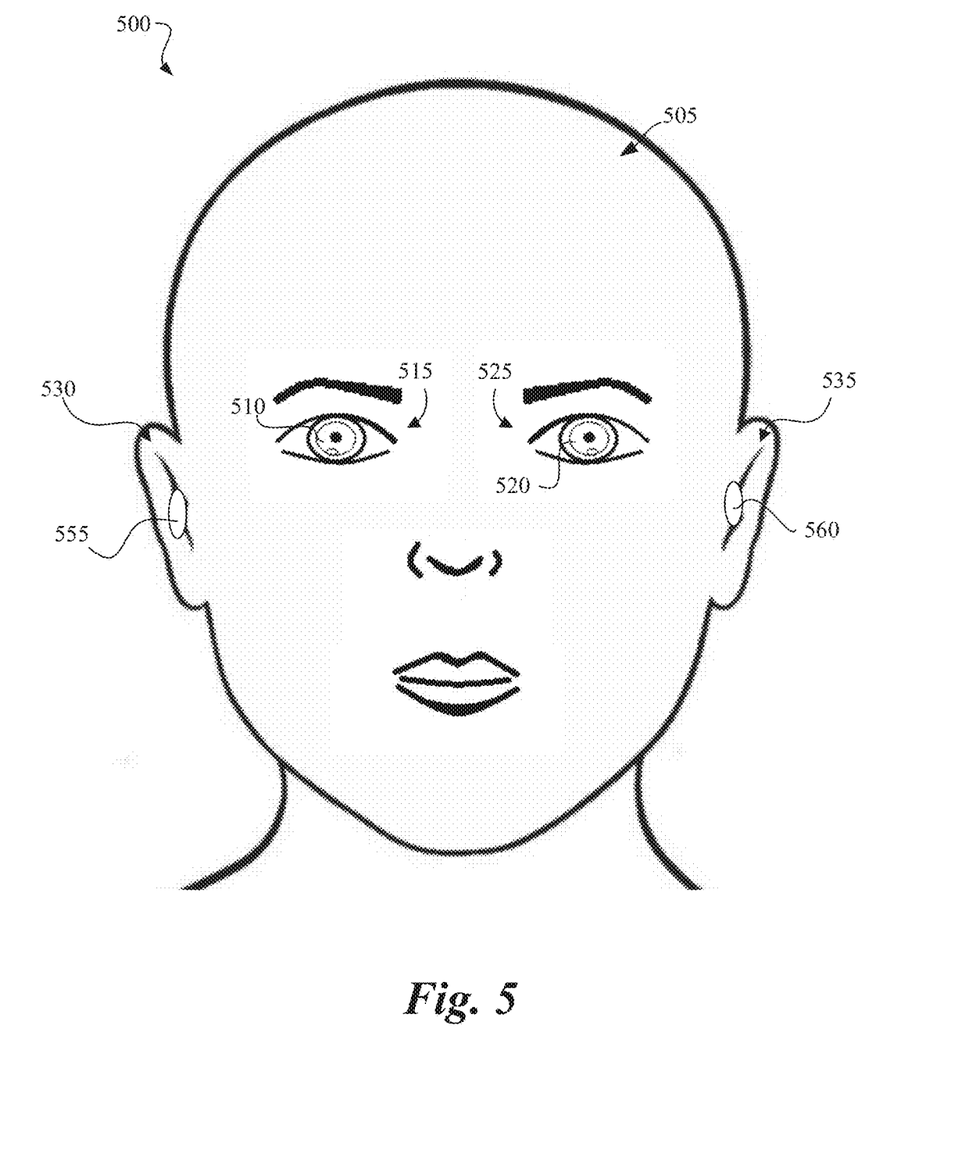
FIG. 5 illustrates an exemplary diagram of a system for controlling ophthalmic devices, in accordance with the present disclosure.

FIG. 5 is a schematic of an example of a system 500 being worn by a user 505. The user 505 can have a first contact lens 510 in a first eye 515 and a second contact lens 520 in a second eye 525. A wireless receiver 555 can be in a first ear 530. In some embodiments, a second wireless receiver 560 can be in a second ear 535. The first contact lens 510 can be a smart contact lens 205 as discussed with reference to FIGS. 2-4. The second contact lens 520 can additionally be a smart contact lens 205.

For example, each contact lens 510, 520 can include a smart contact lens 205 and can detect a biomarker, health condition, ambient condition, or other condition present in the eye of the user 505. The wireless receivers 555, 560 can be in a respective ear closest to the coupling contact lens 510, 520. Having the wireless receiver 555, 560 mountable in or proximate the user's ear 530, 535 can provide a short signal distance between the contact lens 510, 520 and the wireless receiver 555, 560. In some embodiments, the distance can be less than six inches. In some embodiments, the distance can be five inches or less. The distance varies very little as the user's eye and focus change. As long as the contact lenses 510, 520 are in use, the distance is predictable with in a relative range. The predictable, constant distance provides predictability in the desired strength of the signal from the contact lenses 510, 520 to the wireless receivers 555, 560. Having a wearable wireless receivers 555, 560 also provides that the receivers 555, 560 remains within the predetermined distance. The wireless receivers 555, 560 are in a fixed location, in the user's ears 530, 535, relative to the contact lenses 510, 520. The wireless receivers 555, 560 can be located in other locations on the user. For example, there can be a wireless receiver such as an ear piece, wearable watch, a pin, a clip, a necklace, an earring, or the like.

The wireless receiver 555, 560 can alert the user to an unhealthy condition and/or can transmit a message to a device associated with the user. For example, the wireless receiver 555, 560 can transmit a message to a mobile device or other device associated with the user. The wireless receivers 555, 560 can have a longer data range to send out communications farther. This can enable the user to have a pointed alert should the user not hear or receive the message in their ear or other location. In some embodiments, the wireless receiver 555, 560 can communicate or cause to communicate the message to a network of people. For example, if the condition is a safety hazard or potentially dangerous to the user, the wireless receiver 555, 560 can transmit a message to the mobile device to contact the user's emergency contact list. This can enable the emergency contact to confirm the safety and well-being of the user. For example, if the user is a diabetic and is undergoing diabetic shock and has collapsed, the mobile device can trigger the user's emergency contact system of the condition and the location of the user. Alternatively, data collected by the contact lenses 510, 520 can be transmitted to the wireless receiver 555, 560, and subsequently to a healthcare provider, an optometrist or ophthalmologist, a contact lens manufacturer, a parent, and/or an emergency responder.

In some embodiments, both contact lenses 510, 520 are smart contact lenses 205 and provide a dual detection system for the same predetermined condition or factors. In other embodiments, each contact leans 510, 520 can be a smart contact lens 205 but can detect different indicators. For example, one contact lens 510 can detect glucose for a diabetic while the other contact lens 520 can sample for glaucoma or general health indicators, or the like. In some embodiments, if the user has a preexisting condition, such as HIV or other auto immune deficiency, one or both of the contact lens 510, 520 can detect the presence of an illness or indicator of an illness setting in. Each contact lens 510, 510 can individually detect one or more indicators and can both detect the same or can detect different indicators to provide a more holistic diagnostic approach.

Similarly, each contact lens 510, 520 can carry the same substance to distribute to the user or can carry different substances if the user requires it. For example, each contact lens 510, 520 can include a dose of insulin. This can enable the system 500 to inject one or both sets of insulin into the user depending upon the glucose concentrations present. In other embodiments, the user can require different or alternative medication for a variety of environmental and medical conditions.

Figure 6:
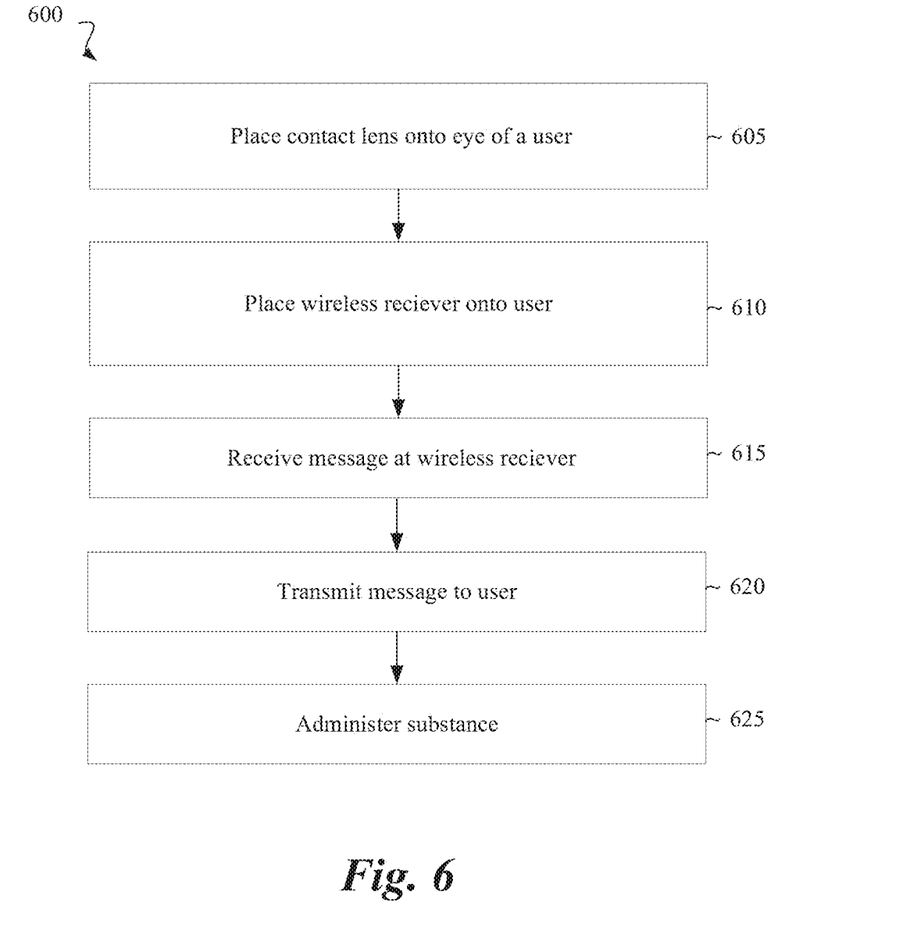
FIG. 6 illustrates an exemplary flow chart of a method for communicating with an ophthalmic device, in accordance with the present disclosure.

FIG. 6 illustrates an example of a method 600 of using a smart system. In this example, the method 600 includes placing 605 a contact lens onto an eye of a user, placing 610 the wireless receiver onto user, and receiving 615 a message at the wireless receiver, transmitting 620 a message to the user, and administering 625 a substance.

At block 605, the contact lens is placed on the eye of a user. At block 610, the wireless receiver is placed onto the user. The wireless receiver can be placed in the ear of the receiver as an earbud or can be another type of wearable device. For example, the wireless receiver can include a smart earring that can be proximate a user's ear. The device can be wearable as a necklace or as a watch or bracelet. In some embodiments, the device can be a ring or a broach or pin that the user can place on their clothing. At block 615, the method 600 can include receiving a message. For example, a sensor proximate the contact lens can detect specific levels of biomarkers indicative of select conditions. Once a predetermined threshold is reached, the sensor can trigger the smart contact lens to transmit a message to the wireless receiver. The wireless receiver can then indicate the unhealthy condition to the user. The sensor can also determine other conditions such as ambient conditions, lighting conditions, temperature, humidity, friction, lens position, or the like. The smart contact lens can transmit the message to the user.

In some embodiments, at block 620, the wireless receiver can transmit a message to the user. In some embodiments, the message can be an audible noise in the user's ear. In other embodiments, the wireless receiver can vibrate or provide another tactile response. In some embodiments, the wireless receiver can transmit a message to a device associated with the user. In further embodiments, the wireless receiver can transmit a message back to the user via the smart contact lens. For example, the wireless receiver can transmit a message to a user communication device (e.g., user communication device 240) embedded in the smart contact lens. The user communication device can flash a message in the user's eyesight. The message can be written, coded, animated, drawings, or other methods of communication. In some embodiments, if the user is wearing two smart contact lens, the alert can transcribe to the detected eye or both eyes.

In some embodiments, if a health alert is present in one eye and a message is transmitted to the wireless receiver, the wireless receiver can communicate with either a second wireless receiver or the second contact lens if the user only has one wireless receiver. For example, if both contact lens detect glucose, and one contact lens detects a high level of glucose, the wireless receiver can ping the second smart contact lens or the second wireless receiver to determine if the second smart contact lens also detects the glucose concentrations. This can provide a check before the user administers insulin.

For example, at block 625, the method can include administering a substance to the user. For example, the smart contact lens can include an output device (e.g. output device 235). The output device can include a substance which can address one or more detected health concerns. For example, the substance can be insulin to counter a high glucose concentration. The substance can be a hydrating substance to counter dry eyes. The substance can be a narcotic or a pain reliever to counter pain. In some embodiments, the substance can be related to any combination of a multitude of diseases including, but in no way limited to, thyroid irregularities, cancers, dry eyes, glaucoma, and conjunctivitis.

Figure 7:
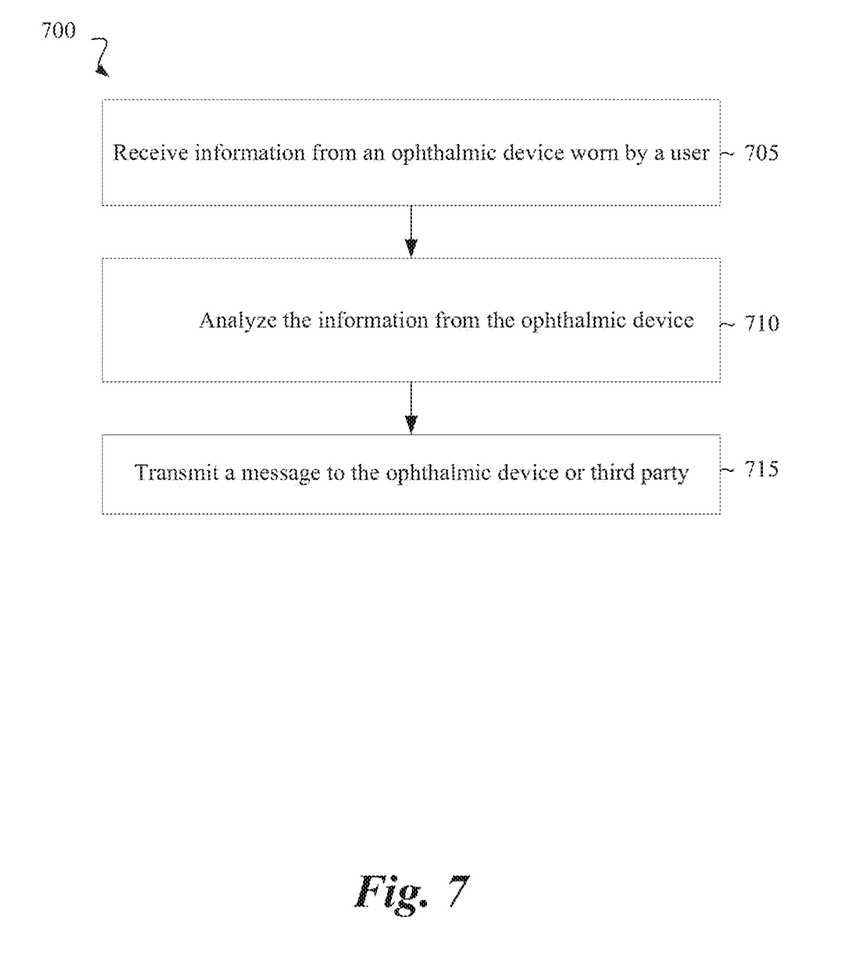
FIG. 7 illustrates an exemplary flow chart of a method for communicating with an ophthalmic device, in accordance with the present disclosure.

FIG. 7 illustrates an example of a method 700 of alerting a user. In this example, the method 700 includes receiving 705 information from an ophthalmic device worn by a user, analyzing 710 the information from the ophthalmic device, and transmitting 715 a message to the ophthalmic device and/or to a third party.

For example, at block 705 the method 700 can receive information from an ophthalmic device worn by a user. The information can be raw data and can be directly transmitted to a wireless receiver. The raw data could involve a number of factors detected by one or more sensors proximate the ophthalmic device. The ophthalmic device can be a contact lens.

At block 710, the method 700 can include analyzing 715 the information. The information can include glucose reading, health condition, eye dryness level, eye strain level or the like. The information can be analyzed to determine what the specific raw data indicates. In some embodiments, the raw data can be analyzed to determine if certain thresholds are satisfied. For example, if the user is diabetic, the method 700 can analyze 710 the information to determine if a glucose concentration has reach an unhealthy threshold.

At block 715, the method 700 can include transmitting a message to the ophthalmic device and/or a third party regarding the analyzed information. In some embodiments, the message can trigger a change of an optical characteristic of the ophthalmic device. For example, the ophthalmic device can be include a user communication device (e.g. user communication device 240). The user communication device can display a message in the user's line of sight. The message can be written words, images, or the like. The message can indicate if a threshold is or is not satisfied. For example, if the user is a diabetic, the message can indicate a glucose concentration. In some embodiments, a specific concentration can be communicated. In other embodiments, a basic yes/no or above/below a predetermined threshold can be communicated. If action is required, the method can transmit information regarding the data and one or more predetermined actions the information necessitates. In some embodiments, the method 700 can request one or more inputs from the user regarding the data. For example, if the user's glucose concentration is above a healthy threshold, the method 700 can request permission to administer an insulin treatment. In other embodiments, the treatment can be automatic and the method 700 can communicate the treatment to the user. In some embodiments, if the information indicates the user is straining to read or if it is too bright or too dark, the method 700 can trigger a change of the ophthalmic device. For example, the method 700 can change a prescription of the ophthalmic device or can trigger a change in the opaqueness of the ophthalmic device. Alternatively, a message regarding the analyzed information can be sent to a medical professional to be analyzed for treatment purposes, such as for the use of an ortho-K lens; to a contact lens manufacturer, to inform them of wear and fit parameters; or to an emergency responder, to inform them of a patient's condition.

In some embodiments, the method 700 can include transmitting the analyzed information to a remote device. The remote device can be the user's remote device, a server, a cloud computing device, or a third party.

Figure 8:
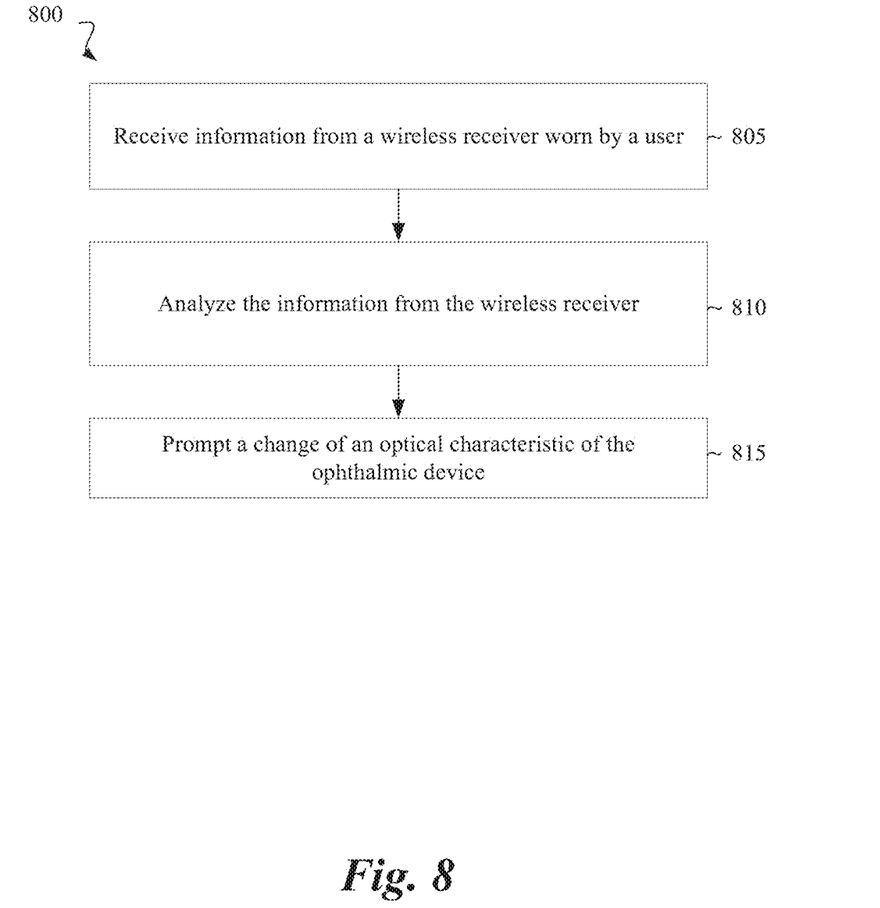
FIG. 8 illustrates an exemplary flow chart of a method for communicating with an ophthalmic device, in accordance with the present disclosure.

FIG. 8 illustrates an example of a method 800 of changing an ophthalmic device. In this example, the method 800 includes receiving 805 information from a wireless device worn by a user, analyzing 810 the information from the wireless receiver, and prompting 815 a change of an optical characteristic of the ophthalmic device.

For example, at block 805, the method 800 can include receiving information from a wireless device worn by a user. The wireless device can include wearable technology. In some embodiments, the wireless device can include an ear piece. The ear piece can be place or worn proximate the user's ear. The ear piece can include one or more accelerometers and other sensors which can detect movement of a user's head.

At block 810, the method 800 can include analyzing the information from the wireless receiver. For example, the method 800 can determine movement of a user's head and specific actions correlating to the user's movement. For example, the user can have their head turned down to read. In other embodiments, the wireless receiver can connect to one or more devices associated with the user, such as, but in no way limited to, a mobile device, a laptop, a computer, a dedicated receiver, or a smart watch. The wireless receiver can receive information that the device is within a predetermined distance to the user and the device is in use indicating the user is currently using their device.

At block 815, the method 800 can include prompting a change of an optical characteristic of the ophthalmic device based on the analyzing. For example, if a user is reading, the method 800 can trigger the ophthalmic device to change a prescription strength to allow the user to read easier. The same might be true if the user is reading or using their remote devices. According to one embodiment, the contact lens can include a contract-able ring, compliant feature, or other shape modification member that, when activated, predictably contracts or otherwise changes the shape, thickness, geometry and/or optical characteristics of the lens.

In some embodiments, the method 800 can also request information from an ophthalmic device to trigger a change. For example, the method 800 can request visual information, health condition information, straining information, biometric information, fit data, movement data, positional data, or other relevant data measurable by the ophthalmic device from the ophthalmic device. The method 800 can then analyze this information and determine if one or more actions need to be taken.

As used herein with reference to contact lenses, the terms 'top' or 'upper' generally refer directionally to the outer surface of the contact lens when worn as intended by a user, while the terms 'bottom' or 'lower' generally refer directionally to the inner surface, or eye-facing surface of the lens. Such terms are used for reference and to aid in the understanding of the present disclosure and are not intended to limit the scope of the present disclosure in any way. For example, as used herein, one embodiment of the exemplary lens describes the variable capacitance sensor being formed on the outer top surface of a contact lens. However, the variable capacitance sensor can be formed on the top, bottom, or inner layer of the lens.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

We claim:

1. A system for communicating with an ophthalmic device, comprising:
   the ophthalmic device including
      a contact lens body,
      a transmitter coupled with the contact lens body, and
      an output device coupled with the contact lens body;
   a sensor coupled to the contact lens body and in communication with the transmitter, wherein the sensor detects at least one of a health condition, an ambient condition, a lens fit, or a biometric data related to the eye; and
   an aural computing system in wireless communication with the ophthalmic device.

2. The system of claim 1, wherein the contact lens further comprises an implantable lens.

3. The system of claim 1, wherein the ophthalmic device comprises:
   an antenna coupled to the contact lens body;
   an energy source in communication with the antenna; and
   a wireless transceiver in communication with the antenna.

4. The system of claim 1, wherein the output device holds a substance to administer to a user when the user is wearing the ophthalmic device; and
   wherein the aural computing system is configured to trigger the output device to administer the substance to an eye of the user in response to a received signal.

5. The system of claim 3, further comprising a user communication device coupled to the contact lens body of the ophthalmic device, the user communication device being configured to change a field of view of a user via a modification of the ophthalmic device.

6. The system of claim 5, wherein the aural computing system is configured to trigger the user communication device to change an optical characteristics of the ophthalmic device.

7. The system of claim 6, wherein changing the optical characteristics of the ophthalmic device comprises displaying a message to the user.

8. The system of claim 6, wherein changing the optical characteristics comprises changing a prescription of the contact lens based on a detected usage.

9. The system of claim 1, wherein the aural computing system further comprises:
   a wearable wireless device including:
      a processor module; and
      an antenna in communication with the processor module;
   wherein the antenna is configured to facilitate communication with the ophthalmic device.

10. The system of claim 1, further comprising:
    a second ophthalmic device;
    wherein the aural computing system is configured to be communicate with the second ophthalmic device.

11. The system of claim 1, further comprising:
    a second ophthalmic device; and
    a second aural computing system configured to communicate with the second ophthalmic device.

12. The system of claim 1, wherein the aural computing system further comprises a wearable device securable to a head of a user.

13. The system of claim 12, wherein the aural computing system further comprises an accelerometer; and
    wherein the accelerometer is configured to detect a movement of the user when the wearable device is worn by the user and in response to a user movement.

14. The system of claim 13, wherein the aural computing system is configured to change the optical characteristics of the ophthalmic device based on detections by the accelerometer.

15. The system of claim 1, wherein the aural computing system is configured to gather and analyze data from the ophthalmic device.

16. The system of claim 15, wherein the aural computing device is configured to transmit data to an external computing system.

17. The system of claim 1, wherein the aural computing device comprises a wearable device.

18. The system of claim 17, wherein the wearable device comprises an ear piece with a predetermined broadcast range.

19. The system of claim 18, wherein the ear piece includes a focused transmitter configured to direct transmissions towards an eye of the user when the ear piece is worn on an ear of the user.

20. A contact lens system comprising:
    a first contact lens including:
       a contact lens body;
       at least one sensor located in the contact lens body of the first contact lens; and
       an output device coupled with the contact lens body and the at least one sensor, wherein the sensor detects at least one of a health condition, an ambient condition, a lens fit, or a biometric data related to the eye; and
    a wearable wireless receiver in communication with the first contact lens.

21. The contact lens system of claim 20, wherein the wearable wireless receiver comprises an ear piece.

22. The contact lens system of claim 20, wherein the first contact lens further comprises:
    a processor module located in the contact lens body of the first contact lens in communication with the at least one sensor; and
    an antenna located in the contact lens body of the first contact lens in communication with the at least one sensor, the antenna having a broadcast range of less than six inches.

23. The system of claim 1, further comprising:
    an ear piece comprising:
       a speaker configured to generate an audible sound; and
       a transmitter configured to communicate with the ophthalmic device.

24. The system of claim 23, wherein the earpiece is configured to transmit instructions to the ophthalmic device to take a measurement using the ophthalmic device.

25. The system of claim 24, wherein the instructions include changing an optical property of the ophthalmic device.

* * * * *